United States Patent
Chinchoy

(10) Patent No.: US 8,398,609 B2
(45) Date of Patent: Mar. 19, 2013

(54) DIASTOLIC CORONARY PERFUSION DETECTION FOR TIMED DELIVERY OF THERAPEUTIC AND/OR DIAGNOSTIC AGENTS

(75) Inventor: Edward Chinchoy, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/115,256

(22) Filed: May 25, 2011

(65) Prior Publication Data

US 2011/0288408 A1 Nov. 24, 2011

Related U.S. Application Data

(62) Division of application No. 10/636,857, filed on Aug. 7, 2003, now Pat. No. 7,951,129.

(51) Int. Cl.
*A61M 31/00* (2006.01)

(52) U.S. Cl. ........... 604/505; 604/503; 604/890.1; 604/891.1

(58) Field of Classification Search ........... 604/890.1, 604/891.1, 115, 268, 503, 505
See application file for complete search history.

(56) References Cited

U.S. PATENT DOCUMENTS

| | | | |
|---|---|---|---|
| 4,531,936 A | 7/1985 | Gordon | |
| 4,822,357 A | 4/1989 | Forster et al. | |
| 4,969,470 A | 11/1990 | Mohl et al. | |
| 5,183,051 A | 2/1993 | Kraidin et al. | |
| 5,188,106 A | 2/1993 | Nappholz et al. | |
| 5,899,927 A | 5/1999 | Ecker et al. | |
| 5,919,210 A | 7/1999 | Lurie et al. | |
| 6,078,834 A | 6/2000 | Lurie et al. | |
| 6,155,267 A | 12/2000 | Nelson | |
| 2002/0151938 A1 | 10/2002 | Corbucci | |
| 2003/0083702 A1 | 5/2003 | Stadler et al. | |

FOREIGN PATENT DOCUMENTS

| | | |
|---|---|---|
| EP | 0 582 162 | 2/2004 |
| WO | WO 03/089033 | 10/2003 |

OTHER PUBLICATIONS

Breithardt et al. "Echocardiographic Quantification of Left Ventricular Asynchrony Predicts an Acute Hemodynamic Benefit of Cardiac Resynchronization Therapy", *J of Am Coll of Cardio.* 2002, vol. 40, No. 3 pp. 536-545.

*Primary Examiner* — Laura Bouchelle
(74) *Attorney, Agent, or Firm* — Reed A. Duthler

(57) ABSTRACT

During diastolic coronary perfusion, blood perfuses through the heart via the coronary arteries. Delivery of a therapeutic and/or diagnostic agent to the heart during diastolic coronary perfusion allows the therapeutic and/or diagnostic agent to efficiently perfuse through the heart. A medical device according to the invention detects closure of the aortic valve of a heart, and initiates delivery of a therapeutic and/or diagnostic agent upon detection of aortic valve closure. The medical device detects aortic valve closure by processing a signal. Exemplary signals used by the medical device to detect aortic valve closure include left or right ventricular accelerometer signals, left or right ventricular flow signals, left or right ventricular pressure signals, aortic pressure signals, pulse pressure signals, systemic arterial pressure signals, electrogram signals, and phonocardiogram signals.

4 Claims, 6 Drawing Sheets

DIASTOLIC CORONARY PERFUSION DETECTION FOR TIMED DELIVERY OF THERAPEUTIC AND/OR DIAGNOSTIC AGENTS

RELATED APPLICATION

This application is a divisional of U.S. patent application Ser. No. 10/636,857, filed Aug. 7, 2003 entitled "DIASTOLIC CORONARY PERFUSION DETECTION FOR TIMED DELIVERY OF THERAPEUTIC AND/OR DIAGNOSTIC AGENTS", herein incorporated by reference in its entirety.

TECHNICAL FIELD

The invention relates to medical devices, and more particularly, to medical devices that deliver therapeutic and/or diagnostic agents to a heart.

BACKGROUND OF THE INVENTION

Various conditions that afflict the heart are treated through delivery of one or more therapeutic and/or diagnostic agents. A variety of techniques involving delivery of biological, genetic, and/or pharmacological therapeutic and/or diagnostic agents to the heart are known for treating conditions such as myocardial infarction (MI), blood clots within the coronary arteries, cardiac arrhythmias, coronary artery disease (CAD), heart failure (HF), or the like. For example, myoblasts, myocytes or stem cells may be delivered to the heart as a therapeutic and/or diagnostic agent to treat an MI (i.e., the death of muscle cells within the heart). As another example, anticoagulants such as warfarin or heparin, or enzymes such as Tissue type plasminogen activator (t-PA), Streptokinase or Urokinase are delivered to the heart to deter or dissolve blood clots within the coronary arteries.

Therapeutic and/or diagnostic agents are delivered into, for example, a chamber of the heart, blood vessels near the heart, such as the aorta, or the pericardial sac of the heart. Typically, therapeutic and/or diagnostic agents are delivered to the heart in the form of a bolus using an infusion apparatus, such as a pump or syringe, coupled to a catheter, and/or a hollow needle. However, it is generally understood that a small percentage (<10%) of a therapeutic and/or diagnostic agent delivered as a bolus actually "perfuses" (e.g., enters the coronary vasculature) of the heart, with the remaining therapeutic and/or diagnostic agent escaping to the systemic circulation.

Consequently, a bolus must include substantially more than a therapeutically effective amount of the therapeutic and/or diagnostic agent, increasing the cost of the treatment, among other disadvantages. Where an implantable drug pump is used to deliver a therapeutic and/or diagnostic agent to the heart, the requirement of excess therapeutic and/or diagnostic agent impacts the size and/or the refilling schedule of a reservoir of a drug pump. Further, the portion of the delivered therapeutic and/or diagnostic agent lost to the systemic circulation may have unintended and potentially undesirable effects on systemic and peripheral tissues of the patient to whose heart the therapeutic and/or diagnostic agent is intended to be delivered.

SUMMARY OF THE INVENTION

In general, the invention is directed to techniques for delivering a therapeutic and/or diagnostic agent to a heart during diastolic coronary perfusion. A medical device detects closure of an aortic valve of the heart, and initiates delivery of the therapeutic and/or diagnostic agent upon detection of the closure of the aortic valve. Because the therapeutic and/or diagnostic agent is delivered timed to the incidence of coronary perfusion, a controlled relative amount of the therapeutic and/or diagnostic agent is allowed to enter the coronary vasculature of the heart, versus being lost to the systemic circulation, such as when delivered using conventional therapeutic and/or diagnostic agent delivery techniques.

Diastolic coronary perfusion occurs upon and for a period of time after the closing of the aortic valve. The aortic valve closes when the pressure in the aorta exceeds the pressure in the left ventricle. After the aortic valve closes the pressure in the aorta increases slightly in response to the closing of the valve. This small increase in pressure forces blood from the aorta into the coronary arteries through the coronary sinus of the heart.

A medical device to deliver a therapeutic and/or diagnostic agent during coronary perfusion includes a sensor to monitor activity within the heart and a processor. The sensor generates a signal that reflects the events of left cardiac or ventricular activity, and the processor processes the signal to detect closure of the aortic valve. The processor controls a pump, which in exemplary embodiments forms a part of the medical device, to deliver the therapeutic and/or diagnostic agent to the heart via a catheter, or the like, at a duration or interval, including simultaneously, timed to aortic valve closure. In exemplary embodiments, the medical device and drug pump are implanted within the patient, and a distal end of the catheter is fluidly coupled to the aorta to deliver the therapeutic and/or diagnostic agent into the aorta and thus, the heart.

In one embodiment, the invention is directed to a method comprising receiving a signal that reflects activity of a heart, processing the signal to detect closure of an aortic valve of the heart, and initiating delivery of a therapeutic and/or diagnostic agent to the heart upon detection of closure of the aortic valve.

In another embodiment, the invention is directed to a medical device comprising a pump to deliver a therapeutic and/or diagnostic agent to a heart via a catheter and a processor. The processor receives a signal that reflects activity of the heart, processes the signal to detect closure of an aortic valve of the heart, and controls the drug pump to deliver the therapeutic and/or diagnostic agent to the heart upon detection of closure of the aortic valve.

In another embodiment, the invention is directed to a system comprising a catheter, a pump to deliver a therapeutic and/or diagnostic agent to a heart via the catheter, a sensor to generate a signal that reflects activity of the heart, and a processor to receive the signal. The processor processes the signal to detect closure of an aortic valve of the heart, and controls the pump to deliver the therapeutic and/or diagnostic agent to the heart upon detection of closure of the aortic valve.

In another embodiment, the invention is directed to a computer-readable medium containing instructions. The instructions cause a programmable processor to receive a signal that reflects activity of a heart, process the signal to detect closure of an aortic valve of the heart, and control a pump to deliver a therapeutic and/or diagnostic agent to the heart upon detection of closure of the aortic valve.

In another embodiment, the invention is directed to a system comprising means for detecting activity within a heart and generating a signal as a function of the activity, means for delivering a therapeutic and/or diagnostic agent to the heart, and means for processing the signal to detect closure of an aortic valve of the heart and controlling the delivery means to deliver the therapeutic and/or diagnostic agent upon detection of closure of the aortic valve.

By example, and without limitation, a diagnostic agent may include a bolus, droplet(s) or stream of a contrast media used in conjunction with a machine vision system such as a fluoroscope and the like, or a dye or other fluid that adheres to or is metabolized to a perceptible state in the presence of one or more tissue, metabolic or fluid flow irregularities. In the event that a contrast media is dispensed a delivery catheter may be utilized that having manually-timed contrast media delivery or an external contrast media pump synchronized to the cardiac cycle via telemetry, wired connection, or the like.

The details of one or more embodiments of the invention are set forth in the accompanying drawings and the description below. Other features, objects, and advantages of the invention will be apparent from the description and drawings, and from the claims.

DETAILED DESCRIPTION OF THE DRAWINGS

Figure 1:
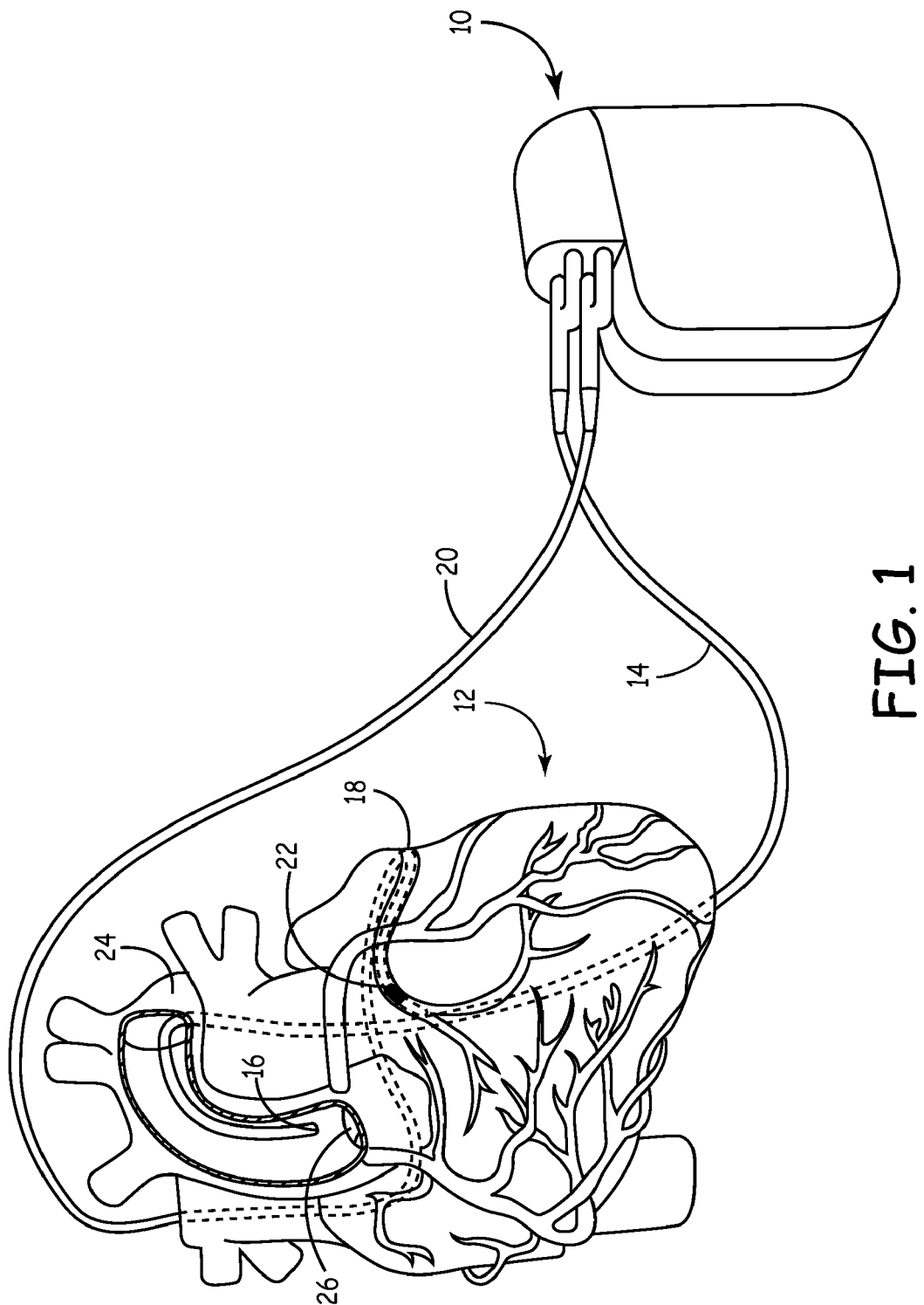
FIG. 1 is a conceptual diagram illustrating an exemplary medical device that delivers a therapeutic and/or diagnostic agent to a heart according to the invention.

FIG. 1 is a conceptual diagram illustrating an exemplary therapeutic and/or diagnostic agent delivery device 10 that delivers a therapeutic and/or diagnostic agent to a heart 12 according to the invention. In exemplary embodiments, as shown in FIG. 1, device 10 is implanted within a patient (not shown). However, in some embodiments, therapeutic and/or diagnostic agent delivery device 10, or components thereof, reside(s) outside of the body of the patient.

Therapy delivery device 10 includes an infusion apparatus 14, e.g., a catheter that provides a conduit for delivery of a therapeutic and/or diagnostic agent, e.g., one or more biological therapeutic and/or diagnostic agents, genetic therapeutic and/or diagnostic agents, and/or pharmaceutical therapeutic and/or diagnostic agents, to a heart 12. In the illustrated embodiment, a distal end 16 of infusion apparatus 14 is positioned within, and/or fluidly coupled to a vessel, or port formed in a vessel, such as a portion of the aorta 24 of heart 12, and device 10 dispenses a precisely timed bolus or dose of at least one therapeutic or diagnostic agent to aorta 24. In such embodiments, a physician manipulates infusion apparatus 14 into fluid communication with an artery, such as the jugular or femoral arteries, and guides distal end 16 to the aorta. In other embodiments, distal end 16 is implanted into the coronary sinus 18 of heart 12 via the great vein or branches thereof. In some embodiments, distal end 16 includes a needle, which can be retractable, to facilitate pericardial therapeutic and/or diagnostic agent delivery.

Therapeutic and/or diagnostic agent delivery device 10 includes a sensor 22 to detect closure of an aortic valve 26 of heart 12, and delivers one or more therapeutic and/or diagnostic agents via infusion apparatus 14 upon detection of the closure. Sensor 22 generates a signal as a function of the activity of heart 16, e.g., the mechanical contractions and/or electrical depolarizations of heart 16. In various embodiments, sensor 22 takes the form of a microphone, a flow sensor, an accelerometer, a pressure sensor, an oximeter, or the like. Device 10 processes the signal generated by sensor 22 to detect closure of aortic valve 26.

In the illustrated embodiment, sensor 22 is carried on a lead 20 and positioned within coronary sinus 18 along a left ventricular free wall of heart 12. In exemplary embodiments where sensor 22 is positioned as illustrated, sensor takes the form of an accelerometer that senses motion of and vibration within the free wall of the left ventricle. In this regard, co-pending non-provisional U.S. patent application Ser. No. 10/377,207 filed on 28 Feb. 2003, invented by Edward Chinchoy and entitled, "METHOD AND APPARATUS FOR OPTIMIZING CARDIAC RESYNCHRONIZATION THERAPY BASED ON LEFT VENTRICULAR ACCELERATION" is hereby incorporated by reference herein. In some embodiments, sensor 22 takes the form of an accelerometer positioned within a right ventricle, atria or is mechanically coupled to a portion of septal wall tissue of a heart. In this regard, co-pending non-provisional U.S. patent application Ser. No. 10/631551 filed on 30 Jul. 2003, invented by Robert Nehls and Todd Sheldon and entitled, "METHOD OF OPTIMIZING CARDIAC RESYNCHRONIZATION THERAPY USING SENSOR SIGNALS OF SEPTAL WALL MOTION" is hereby also incorporated by reference herein. Suitable accelerometers for the practice of the invention include piezoceramic accelerometers, among many others known and/or used in the cardiac pacing arts.

The invention is not however limited to embodiments where sensor 22 takes the form of an accelerometer. For example, in some embodiments, sensor 22 comprises a pressure sensor implanted in the aortic arch to measure the aortic pressure, the left ventricle to measure left ventricular pressure, pulse pressure, the right ventricle to measure right ventricular pressure, or the systemic arteries to measure arterial pressure. In other embodiments, sensor 22 takes the form of a similarly positioned flow sensor or oximeter. In some embodiments, a pressure, flow, or oximetery sensor 22 is implanted in the left ventricle by accessing the right ventricle and puncturing the intraventricular septum of heart 12.

In some embodiments, sensor 22 takes the form of a vibration sensor, e.g. a microphone, that generates a signal that includes vibration associated with the closure of aortic valve 26. Such a sensor 22 can be implanted anywhere within a body of a patient, or positioned on the surface of the patient. In exemplary embodiments, such a sensor 22 is not carried on a lead, but is included within a housing of device 10.

The invention is not limited to the above-identified sensors. Further, the invention is not limited to embodiments where device 10 includes a single sensor 22. Rather, in some embodiments, IMD 10 uses two or more sensors 22 or types of sensors 22 to detect closure of aortic valve 26.

Figure 2:
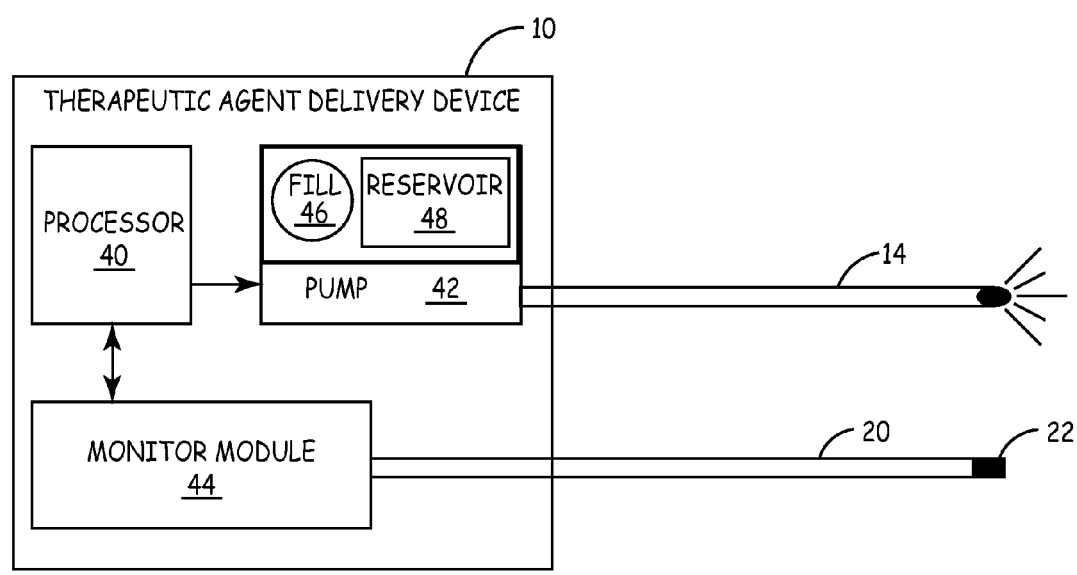
FIG. 2 is a block diagram further illustrating the device of FIG. 1.

FIG. 2 is a block diagram further illustrating device 10 of FIG. 1. As illustrated in FIG. 2, therapeutic and/or diagnostic agent delivery device 10 includes processor 40 that communicates with pump 42 and monitor module 44. Processor 40 takes the form of one or more of a microprocessor, digital signal processor, application specific integrated circuit, field-programmable gate array, and other logic circuitry programmed to provide the functionality ascribed to processor 40 herein. In some embodiments, device 10 includes a memory that stores program instructions. The program instructions control processor 40 to provide the functions ascribed to it herein.

Pump 42 typically includes fill port 46 to facilitate filling and re-filling of reservoir 48. Reservoir 48 holds a therapeutic and/or diagnostic agent or a mixture of therapeutic and/or diagnostic agents. In some embodiments, a therapeutic and/or diagnostic agent delivery device 10 includes one or more pumps 42 to deliver a therapy agent or a mixture of therapy agents stored in one or more reservoirs 48 to a heart via one or more infusion apparatuses 14. However, for ease of illustration, therapy agent delivery device 10, as shown in FIG. 2, includes one of each.

Processor 40 controls pump 42 to create a pressure gradient, thereby forcing the therapeutic and/or diagnostic agent stored in reservoir 48 along infusion apparatus 14. In some embodiments, a distal end of infusion apparatus 14 is implanted near heart 12 (FIG. 1). In exemplary embodiments, infusion apparatus 14 is implanted in the aortic arch, as shown in FIG. 1. Another exemplary implant location, as described above, includes any location fluidly coupled to coronary sinus 18.

As discussed above, in exemplary embodiments the signal generated by sensor 22 includes one of a left or right ventricular accelerometer signal, a left or right ventricular flow signal, an aortic pressure signal, a left or right ventricular pressure signal, a systemic arterial pressure signal, an electrogram signal and a phonocardiogram signal. Upon receiving such a signal, monitor module 44 analyzes the signal to detect closure of the aortic valve. In some embodiments, monitor module 44 applies analog analysis, such as envelope detection, and monitor module 44 includes analog filters, sense threshold circuits and the like to identify the closure of aortic valve 26. In some embodiments monitor module 44 applies digital signal analysis techniques, such as wavelet analysis and/or Fourier transforms, to the signal to identify the closure of aortic valve 26.

In digital signal analysis embodiments of device 10, monitor module 44 converts the signal from an analog signal into a digital signal. In some embodiments, monitor module 44 does not process the digital signal, but instead provides the digital signal to processor 40 for digital signal analysis and detection of closure of aortic valve 26.

Figure 3:
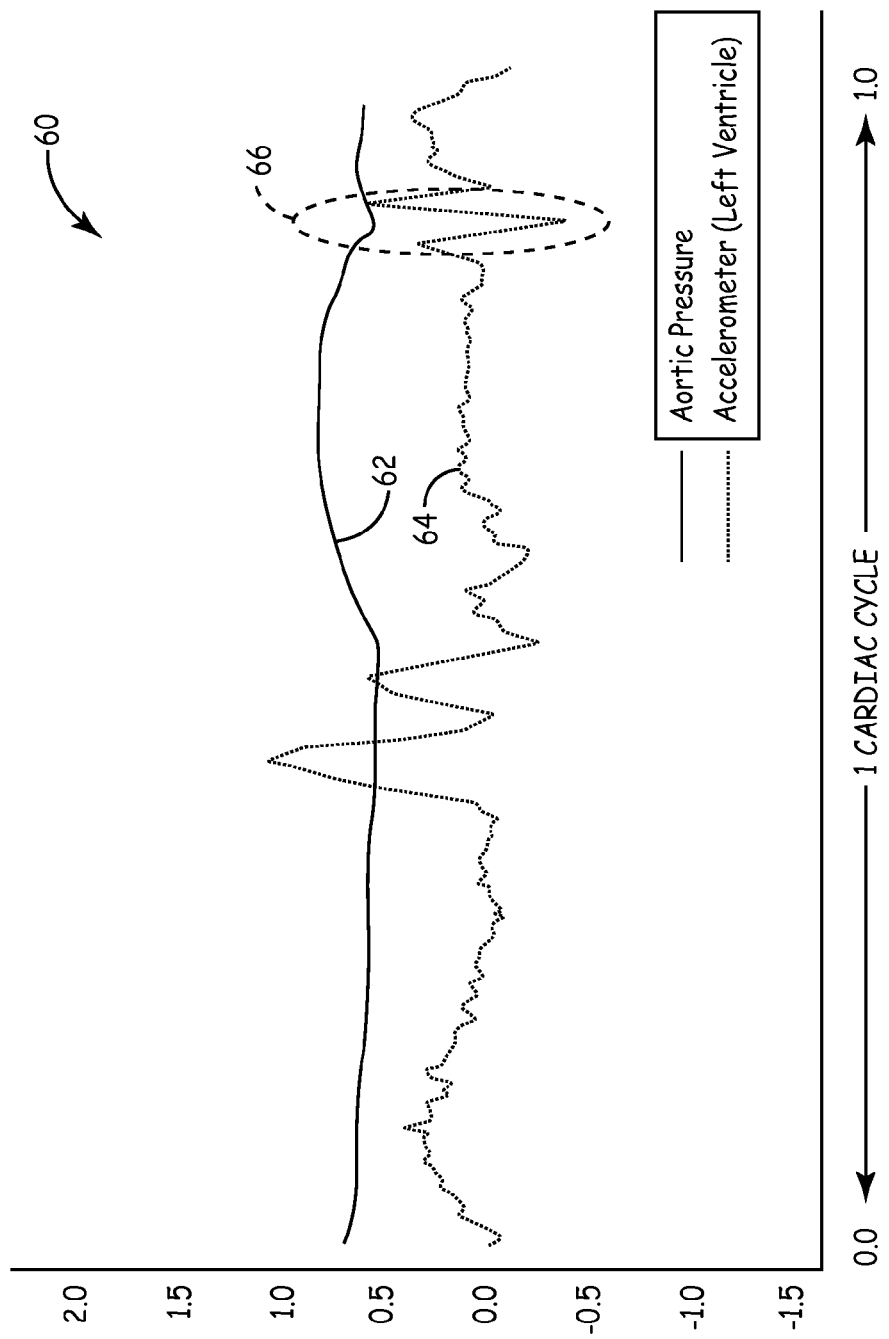
FIG. 3 is a timing diagram illustrating exemplary signals processed by the device of FIG. 1 to detect closure of an aortic valve of the heart.

FIG. 3 is a timing diagram illustrating exemplary signals 62 and 64 processed by device 10 of FIG. 1 to detect closure of aortic valve 26 of heart 16. FIG. 3 depicts signals 62 and 64 over a single cardiac cycle. Region 66 indicates a period of time during which aortic valve 26 closes when onset of diastolic coronary perfusion occurs. A therapeutic and/or diagnostic agent delivery device 10 detects the aortic valve closure by identifying one or more morphological characteristics of signals 62, 64.

Monitor module 44 receives signals 62 and 64 from sensors 22. In the illustrated example, signal 62 is an aortic pressure signal generated by a pressure sensor 22 as a function of the aortic pressure. Further, signal 64 is an accelerometer signal generated by an accelerometer sensor 22 as a function of the motion of the left ventricular wall. In some embodiments, the monitor module converts signals 62, 64 from analog signals to digital signals and delivers the digital signals to processor 40 for monitoring. In other embodiments, monitor module processes the signal to detect aortic valve closure using analog or digital signal processing techniques as discussed above.

As illustrated in FIG. 3, aortic pressure signal 62 comprises fairly constant amplitude for the first half of the cardiac cycle. During this time the heart is in diastole and the aortic valve is closed. Once the heart enters systole the aortic valve opens and blood from the left ventricle is pumped into the aorta increasing the amplitude of aortic pressure signal 62. When the aortic valve closes again and a local minimum occurs within region 66. This local minimum is known as the dicrotic notch and further indicates diastolic coronary perfusion. Processor 40 or monitor module 44 detects this local minimum to detect closure of the aortic value using digital, e.g., Fourier or wavelet, analysis.

Left ventricular accelerometer signal 64 measures the motion of the outer wall of the left ventricle. In some embodiments, a left ventricular accelerometer sensor 22 is implanted via the coronary sinus, as illustrated in FIG. 1, near the left ventricular free wall to facilitate measuring this motion. As the cardiac cycle begins small disturbances are noted that correspond to ventricular filling. As ventricles contract the absolute amplitude of signal 64 increases. At region 66, where closure of aortic valve 26 occurs, the absolute amplitude of signal 64 again increases. Processor 40 or monitor module 44 detects this second amplitude increase using, for example, Fourier or wavelet analysis, or analog envelope detection circuitry, and the like.

In some embodiments where monitor module 44 or processor 40 applies digital signal analysis to identify morphological characteristics of signals 62 and/or 64 associated with aortic valve closure, module 44 or processor 40 compares the signal to a template that includes, for example, local minimums, maximum slopes, minimum slopes, local maximums, or some other fiducial point. Device 10 can further tailor templates using learning algorithms to fit specific patient data, thereby improving accuracy.

In some embodiments, the pump 42 delivers the therapeutic and/or diagnostic agent for a set period of time. The set period of time pertains to heartbeats and various embodiments deliver the therapeutic and/or diagnostic agent in various modes. Exemplary modes include continuous delivery, i.e., delivery every heartbeat and delivery every nth beat. For example, n can equal 5 and thus delivery occurs every $5^{th}$ heart beat. Other exemplary modes enable delivery of the drug based on physiological parameters. For example, a patient with a weak heart requires epinephrine to strengthen cardiac performance. Thus, pump 42 delivers epinephrine based on measures of the strength of the heart. Further embodiments can incorporate modes of delivery where the therapeutic and/or diagnostic agent is delivered according to a schedule stored in a memory.

Figure 4:
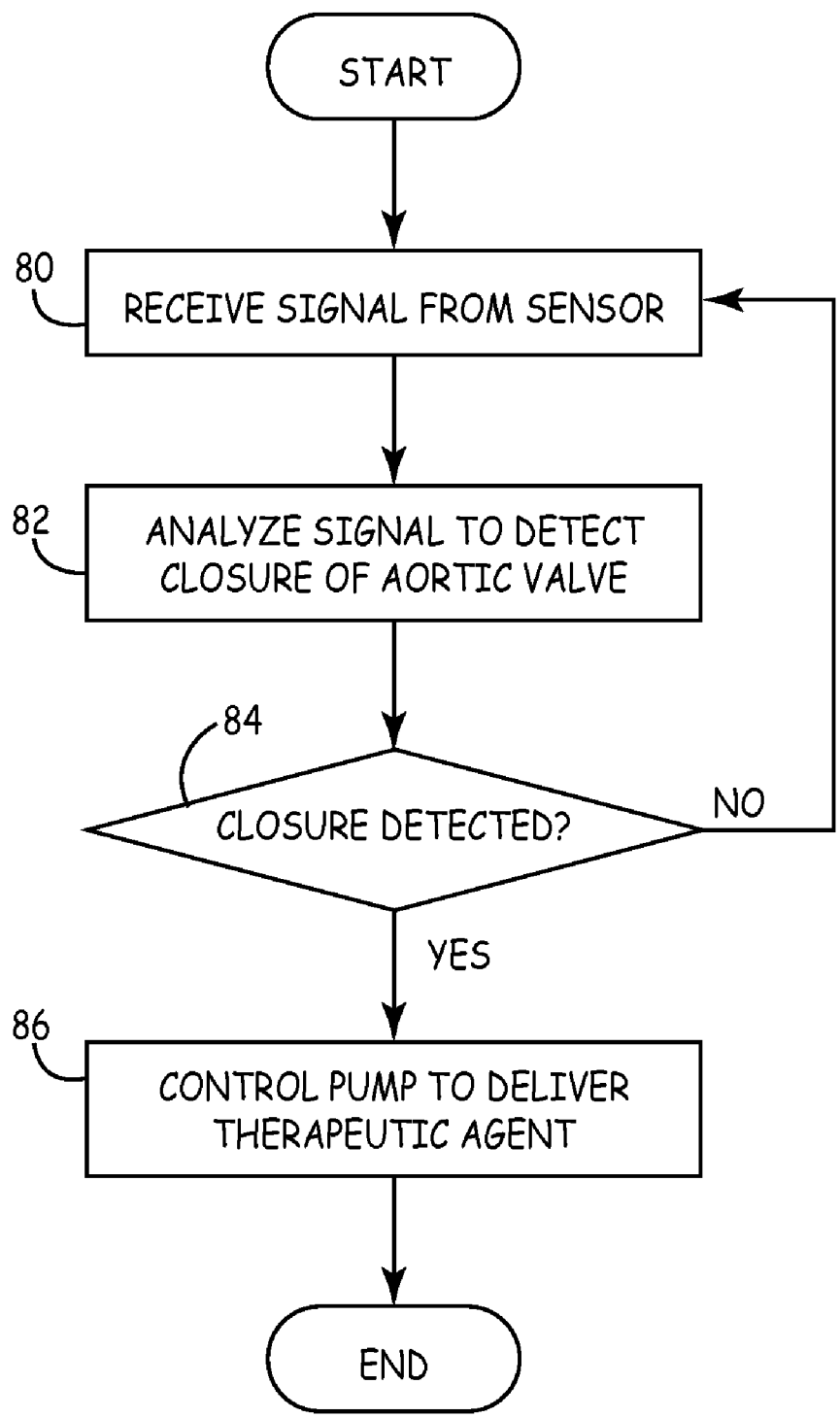
FIG. 4 is a flowchart illustrating an exemplary method employed by the medical device of FIG. 1 to deliver a therapeutic and/or diagnostic agent to the heart.

FIG. 4 is a flowchart illustrating an exemplary method employed by medical device 10 of FIG. 1 to deliver a therapeutic and/or diagnostic agent to the heart. Monitor module 44 receives a left ventricular accelerometer signal from sensor 22 (80), which resembles signal 64 of FIG. 3. Monitor module 44 analyzes the signal to detect closure of aortic valve 26 (82).

In exemplary embodiments described above, monitor module 44 applies analog analysis to detect the closure of aortic valve 26. For example, monitor module 44 can apply envelope detection to the signal to detect closure of aortic valve 26. If monitor module 44 does not detect closure of the aortic valve then monitor module 44 continues to receive and analyze the signal (44).

In the event that monitor module 44 detects the closure of aortic valve 26, module 44 provides an indication to processor 40, which controls pump 42 to initiate delivery of a therapeutic and/or diagnostic agent from reservoir 48 to the heart (86). Delivery of the therapeutic and/or diagnostic agent during diastolic coronary perfusion post aortic valve closure can allow for a controlled relative amount of therapeutic and/or diagnostic agent to perfuse the heart.

Device 10 delivers one or more therapeutic and/or diagnostic agents or mixtures of therapeutic and/or diagnostic agents in accordance with the inventions. In particular, device 10 delivers any one or combination of genetic agents, biological agents and pharmaceutical agents to provide specific therapies to a patient. For example, in some embodiments, device 10 delivers pharmaceutical agents, such as epinephrine and digitalis, to enhance cardiac performance. Other pharmaceutical agents such as t-PC can be delivered to dissolve blood clots in heart 12. Device 10 can further deliver genetic agents to provide therapy for ischemia. For example, device 10 can deliver stem cells to replace dying heart cells.

Figure 5:
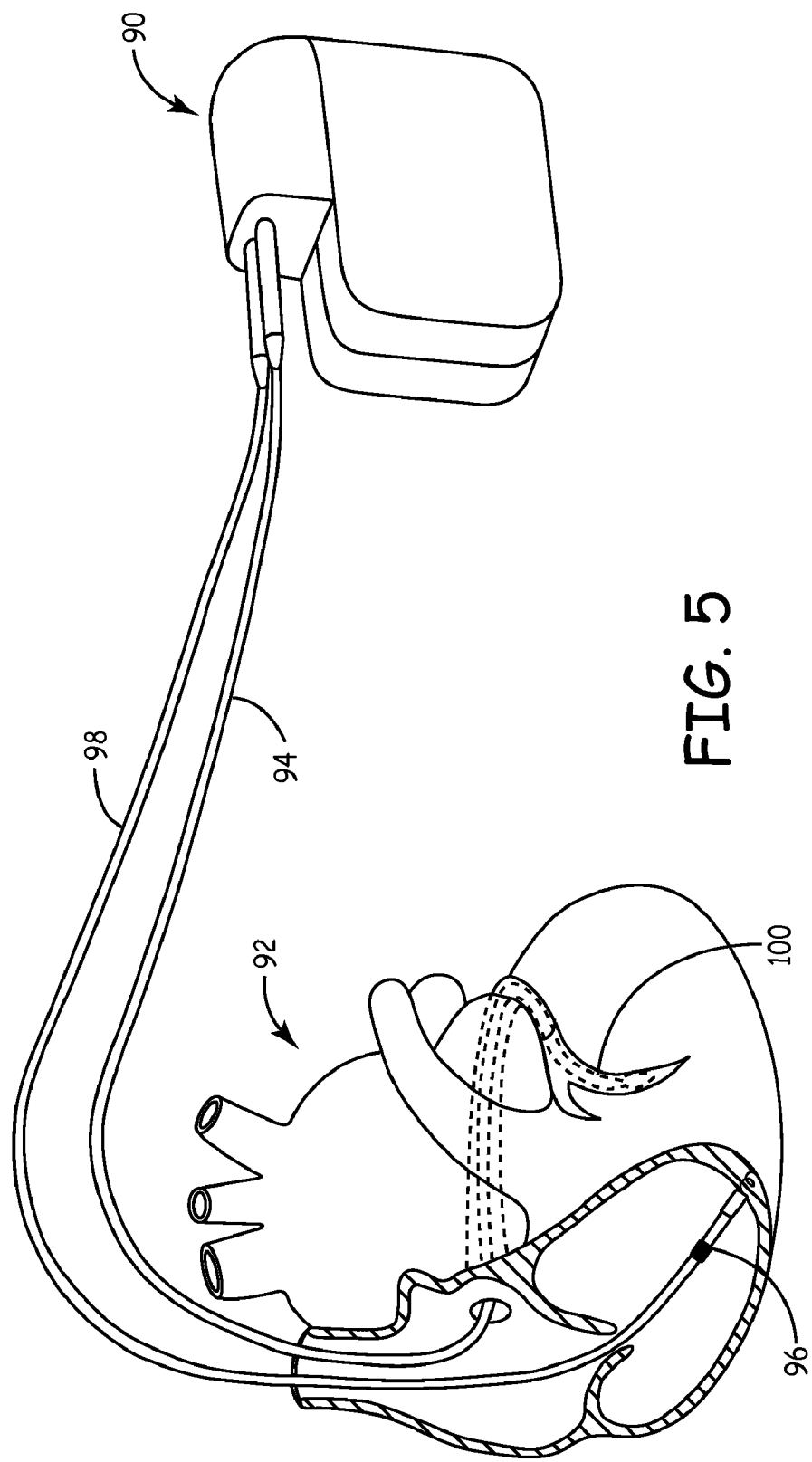
FIG. 5 is a conceptual diagram illustrating another exemplary medical device that delivers a therapeutic and/or diagnostic agent to a heart according to the invention.

FIG. 5 is a conceptual diagram illustrating another exemplary medical device 90 that delivers a therapeutic and/or diagnostic agent to a heart according to the invention. Therapeutic and/or diagnostic agent delivery device 90, as shown in FIG. 5, delivers a therapeutic and/or diagnostic agent to heart 92 via infusion apparatus 94, e.g. a catheter. Furthermore, therapeutic and/or diagnostic agent delivery device 90 receives a signal from sensor 96 via filaments included within lead 98. Based on this signal, therapeutic and/or diagnostic agent delivery device 90 delivers the therapeutic and/or diagnostic agent.

In particular, FIG. 5 illustrates alternative locations for a sensor 96 and distal end 100 of infusion apparatus 94 that are employed according to some embodiments of the invention. Infusion apparatus 94, as shown in FIG. 5, is implanted into the coronary sinus of heart 92. Sensor 96 is inserted into the right ventricle of heart 92. These exemplary implant locations can be selected due to the ease of positioning lead 98 and infusion apparatus 94 in these positions relative to the positions of lead 20 and infusion apparatus 14 illustrated in FIG. 1.

Infusion apparatus 94 delivers a therapeutic and/or diagnostic agent to the coronary arteries, similar to infusion apparatus 14. However, apparatus 94 access the coronary arteries via the right atrium of heart 92. Nonetheless, therapeutic and/or diagnostic agents delivered by device 90 via infusion apparatus 94 perfuse heart 92.

Sensor 96 generates a signal as a function of the acoustics or mechanical motion within the right ventricle of heart 92. Other acoustic locations where sensor 96 can monitor heart 92 include the housing of device 90, the skin surface of patient proximate to heart 92, and the like. Placement of sensor 96, e.g., a microphone, pressure transducer, or accelerometer in either the right or left ventricle provides sensor 96 proximity to heart 92 to facilitate sensing of the noise and/or motion associated with the closure of the aortic valve. Thus this position is viable to monitor heart activity and more particularly the closure of the aortic valve (not shown) of the heart 92.

Figure 6:
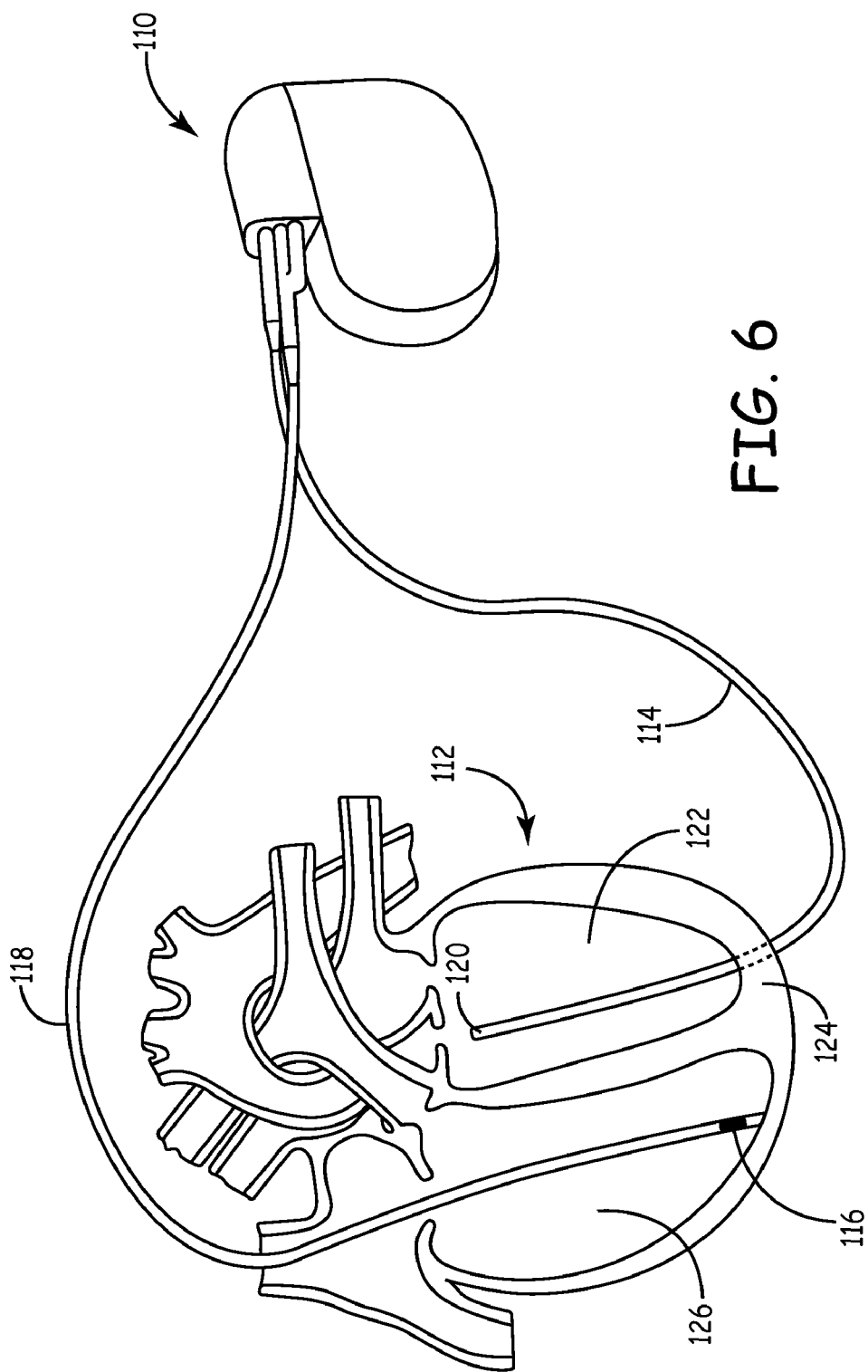
FIG. 6 is a conceptual diagram illustrating yet another exemplary medical device that delivers a therapeutic and/or diagnostic agent to a heart according to the invention.

FIG. 6 is a diagram illustrating another exemplary medical device 110 that delivers a therapeutic and/or diagnostic agent to a heart 112 according to the invention. Therapeutic and/or diagnostic agent delivery device 110, as shown in FIG. 6, delivers a therapeutic and/or diagnostic agent to heart 112 via infusion apparatus 114, which is shown as a catheter. Furthermore, therapeutic and/or diagnostic agent delivery device 110 receives a signal from sensor 116 via filaments included within lead 118. Similar to therapy agent delivery device 90, therapy agent delivery device 110 delivers the therapeutic and/or diagnostic agent based on the signal.

In particular, FIG. 6 illustrates a further alternative location for distal end 120 of infusion apparatus 114 that is employed according to some embodiments of the invention. Infusion apparatus 114, as shown in FIG. 6, is implanted into left ventricle 122 by puncturing a portion of ventricular septal wall tissue or a portion of the apex 124 of heart 112. Other exemplary implant procedures exist to implant distal end 120 into left ventricle 122. For example, distal end 120 can be implanted into right ventricle 126 via the right atrium of heart 112. Once in the right ventricle, distal end 120 of infusion apparatus 114 is inserted into left ventricle 122 via a puncture in the septum between right ventricle 126 and left ventricle 122. A further example of implanting distal end 120 into left ventricle 122 includes inserting distal end 120 into the right atrium of heart 112. Distal end 120 is then inserted into the left atrium of heart 112 via a puncture in the septum between the right and left atrium. From the left atrium, distal end 120 of infusion apparatus 114 is implanted in left ventricle 122.

In some embodiments, distal end 120 of infusion apparatus 114, after being inserted into left ventricle 122, is fed through the aortic valve into the aorta of heart 112. In these embodiments, wherein distal end 120 is implanted into the aorta via left ventricle 122, infusion apparatus 114 delivers a therapeutic and/or diagnostic agent similar to infusion apparatus 14. However, the implant locations differ in that infusion apparatus 14 is implanted via the femoral or jugular arteries, as described above. Nevertheless, therapeutic and/or diagnostic agents delivered by device 110 via infusion apparatus 114 perfuse heart 112. In embodiments where a therapeutic and/or diagnostic agent is delivered to left ventricle 122, a smaller percentage of the delivered therapeutic and/or diagnostic agent may perfuse heart 112 than is possible with direct aortic delivery.

Sensor 116 generates a signal similar to that of sensor 96. The signal represents acoustics or mechanical motion, or both acoustics and mechanical motion of heart 112. Similar to sensor 96, locations of sensor 116 include the housing of device 110, on the skin of the patient proximal to heart 112, within heart 112, as shown by FIG. 6, and the like. Placement of sensor 116, which includes similar sensor types as sensor 96 listed above, in either the right or left ventricle provides sensor 116 proximity to heart 112 to facilitate detection of the closure of the aortic valve.

The invention as described above provides for the efficient delivery of a therapeutic and/or diagnostic agent to a heart. In particular, a therapeutic and/or diagnostic agent delivery device in accordance with the invention may delivery a therapeutic and/or diagnostic agent such that a majority of the therapeutic and/or diagnostic agent perfuses the heart. Moreover, the therapeutic and/or diagnostic agent delivery device may ensure this by detecting the closure of the aortic valve and delivering the therapeutic and/or diagnostic agent during diastolic coronary perfusion. A number of embodiments are described above that illustrate therapeutic and/or diagnostic agent delivery devices in accordance with these techniques.

Various embodiments of the invention have been described. However, one skilled in the art will appreciate that various medications can be made to these embodiments without departing from the scope of the invention. For example, although described herein in the context of a single device, a device according to the invention can include components, e.g., a pump, a processor, and/or a sensor; one or more of which may be disposed external to the body. In some embodiments, a catheter and/or lead percutaneously access a position within a patient. For example, in some embodiments and external device according to the invention could be used to perfuse the heart with a therapeutic and/or diagnostic agent during a stay in a hospital. Finally, all forms of therapeutic and/or diagnostic agents are intended to benefit from the teaching of the present invention, including without limitation such agents when rendered at an appropriate viscosity or when diluted in a fluid medium, and the like. These and other embodiments are within the scope of the following claims.

The invention claimed is:

1. A non-transitory computer-readable medium comprising instructions that cause a programmable processor to:
   receive a signal that reflects activity of a heart;
   process the signal to detect closures of an aortic valve of the heart; and
   control a pump to deliver a therapeutic and/or diagnostic agent to the heart responsive to a plurality of the detections of aortic valve closures by delivering controlled amounts of the therapeutic and/or diagnostic agent over the series of heartbeats, during time periods in which aortic pressure increases responsive to closures of the aortic valve.

2. The computer-readable medium of claim 1, wherein the instructions that cause a programmable processor to process the signal further comprise instructions that cause a programmable processor to process at least one of a ventricular accelerometer signal, a ventricular flow signal, a ventricular pressure signal, an aortic pressure signal, a systemic arterial pressure signal, an electrogram signal, a phonocardiogram signal.

3. The computer-readable medium of claim 1, wherein the instructions that cause a programmable processor to process the signal further comprise instructions that cause a programmable processor to digitally process the signal.

4. The computer-readable medium of claim 3, wherein the instructions that cause a programmable processor to digitally process the signal further comprise instructions that cause a programmable processor to digitally process a pressure signal to detect a dichrotic notch within the signal.

* * * * *